United States Patent [19]

Piechota, Jr.

[11] 4,401,648

[45] Aug. 30, 1983

[54] DENTAL CREAM COMPOSITION

[75] Inventor: Stanley E. Piechota, Jr., Somerset, N.J.

[73] Assignee: Colgate-Palmolive Company, New York, N.Y.

[21] Appl. No.: 363,328

[22] Filed: Mar. 29, 1982

[51] Int. Cl.³ .............................................. A61K 7/16
[52] U.S. Cl. ..................................................... 424/49
[58] Field of Search .................................... 424/49-58

[56] References Cited

U.S. PATENT DOCUMENTS

| | | | |
|---|---|---|---|
| 3,670,076 | 6/1972 | Muhler | 424/49 |
| 3,862,307 | 1/1975 | Di Giulio | 424/52 |
| 4,042,680 | 8/1977 | Muhler et al. | 424/55 |
| 4,064,231 | 12/1977 | Asakawa et al. | 424/52 |
| 4,081,526 | 3/1978 | Asakawa et al. | 424/57 |
| 4,108,979 | 8/1978 | Muhler et al. | 424/49 |
| 4,108,981 | 8/1978 | Muhler et al. | 424/55 |
| 4,254,101 | 3/1981 | Denny | 424/52 |
| 4,314,990 | 2/1982 | Denny et al. | 424/52 |

*Primary Examiner*—Shep K. Rose
*Attorney, Agent, or Firm*—Robert L. Stone; Murray M. Grill; Herbert S. Sylvester

[57] ABSTRACT

Dental cream which readily disperses when agitated in the presence of water or saliva. The gel system of the dentifrice contains xanthan and an alginate in a weight ratio of about 3:1 to 1:3, preferably about 3:1 to 1:1. The dental cream also has desirable texture or "feel" in the mouth and undergoes slow drainage of liquid from foam produced during toothbrushing.

4 Claims, No Drawings

DENTAL CREAM COMPOSITION

This invention relates to a dentifrice which readily disperses upon mild agitation in the presence of an aqueous medium, such as during toothbrushing in the presence of saliva. It also provides other desirable characteristics such as a pleasant texture or "feel" in the oral cavity during toothbrushing and loses liquid from its foam only slowly.

In U.S. Pat. No. 4,254,101 a dental cream is described which contains a carboxyvinyl polymer as binding agent in combination with high humectant (about 30–70% by weight on a pure humectant basis) and a silica abrasive. Xanthan may also be present as an additional binding agent.

Xanthan is a pseudoplastic material which tends to contribute a stringy, difficult-to-disperse quality to dentifrices which contain it. Accordingly, dental creams containing mixtures of carboxyvinyl polymer and xanthan in a dental cream may have an undesirable stringy appearance, particularly when at least about half of the binding agent mixture is xanthan. In fact, when at least about half of a xanthan-carboxyvinyl polymer mixture is xanthan, the pseudoplastic viscosity properties are similar to those with xanthan alone.

Alginates such as sodium alginate are known as binding agents too. They have low pseudoplastic viscosity characteristics similar to those of carboxyvinyl polymers. Quite unexpectedly, it has been found that mixtures of xanthan and alginate binding agent have pseudoplastic viscosity properties which provide desirable non-stringy, easy dispersion character to dental creams containing xanthan and alginate in a broad ratio to each other while also providing desirable texture or "feel" when dispersed in the oral cavity.

Xanthan has been proposed for use in dentifrice type compositions in British Pat. Nos. 1,372,382; 1,425,922; Japanese published application No. 7277/67; Japanese published application No. 28162/72; U.S. Pat. No. 4,081,526; and British published application No. 20 82 062; as well as in commonly assigned pending U.S. application Ser. No. 299,684, filed Sept. 8, 1981. In U.S. Pat. No. 4,065,578 a chewing gum is described in which xanthan or alginates are alternative colloids for use in the gum base.

It is an advantage of this invention that a dental cream is provided which is easily dispersible into the oral cavity during toothbrushing.

It is a further advantage of this invention that a dental cream is provided which has a highly desirable texture or "feel" upon dispersion in the oral cavity.

It is a further advantage of this invention that a dental cream is provided which only slowly loses liquid from foam produced during tooth brushing. Other advantages will be apparent from consideration of the following specification.

In accordance with certain of its aspects, this invention relates to a dental cream comprising about 20–80% by weight of a liquid vehicle phase comprising water and humectant and about 0.2–5% by weight of a gel vehicle phase and dispersed therein about 10–75% of a water-insoluble dentally acceptable polishing agent, said vehicle containing a weight ratio of about 3:1 to 1:1 of xanthan to alginate salt.

Xanthan gum is a fermentation product prepared by action of the bacteria of the genus Xanthomonas upon carbohydrates. Four species of Xanthomonas, viz. *X. campetris, X. phaseoli, X. malvocearum* and *X. carotae* are reported in the literature to be the most efficient gum producers. Although the exact structure is not determined, it is generally accepted to be a heteropolysaccharide with a molecular weight of several million. It contains D-glucose, D-mannose, and D-glucoronic acid in molar ratio of 2.8:3:2.0. The molecule contains 4.7% acetyl and about 3% pyruvate. The proposed chemical structure configuration can be found in McNeely and Kang, Industrial Gums, ed. R. L. Whistler, Ch. XXI, 2nd Edition, New York, 1973. The procedure for growing, isolating and purifying the xanthan gum is found in Manufacturing Chemist, May 1960, pages 206–208 (including mention at page 208 of potential use of gums therein described for formulating toothpastes).

Use of special grades of xanthan gum, such as described in U.S. Pat. No. 4,263,399 are within the scope of this invention. A grade described in U.S. Pat. No. 4,263,399 is a xanthan gum in which up to about 1.6% of the carboxyl groups are bound to calcium and the remaining carboxyl groups are bound to sodium, potassium, a mixture of sodium and potassium or other non-calcium cations.

The alginate salt in the vehicle may be any orally acceptable non-toxic alginate such as those selected from the group consisting of alkali group alginates such as sodium, potassium and ammonium alginates and lower alkylene glycol alginates such as propylene glycol alginate. The alginate salt may range in molecular weight from about 4000 to about 180,000.

Alginates are derived from giant kelp. The alginate salts are typically low calcium sodium alginates (for example KELCOGEL LV, KELCOSOL and KELTONE, all trademarks of KELCO Company), as well as sodium alginates, ammonium alginates, potassium alginates, propylene glycol alginates and the like.

The preferred alginate salt in said vehicle is low-calcium sodium alginate with a molecular weight ranging from about 80,000 to about 200,000 say about 180,000.

The most preferred alginate salt is a high-viscosity, specially clarified, low calcium sodium alginate such as the KELCOSOL brand manufactured by the Kelco division of Merck & Co., Chicago, Ill.

Information regarding alginate salts is described in the booklet "Kelco Algin/Hydrophilic Derivatives of Alginic Acid for Scientific Water Control," Second Edition, 1977, Kelco Division of Merck & Company, Chicago, Ill.

The weight ratio of xanthan to alginate salt in the gelling agent mixture is about 3:1 to 1:3 of xanthan to alginate salt, preferably about 3:1 to 1:1 of xanthan to alginate salt. The gelling agent mixture comprises about 0.2–5% by weight of the dental cream, preferably about 0.5–5%, most preferably about 0.5–2%.

A thickener agent such as silica aerogel may also be included, typically in an amount of 5 to 10% by weight.

The liquid phase, proportioned with the xanthan-alginate mixture to give a creamy or gel character, comprises water and humectant, such as sorbitol, typically commercially available in 70% aqueous solution, glycerine, low molecular weight polyethylene glycol (e.g. about 200 to 600) or propylene glycol. The total liquid content of the dental composition is generally from 20 to 80% by weight.

The dental composition further comprises a dentally acceptable water insoluble polishing material. Examples of polishing materials are water-insoluble siliceous polishing agent, hydrated alumina and dicalcium phosphate (including dihydrated calcium phosphate and anhydrous dicalcium phosphate). Siliceous polishing agents include colloidal silica xerogel, precipitated silica and sodium aluminosilicates or silica grades containing combined alumina, typically in amount of about 0.1-7% by weight. Other polishing materials include insoluble sodium metaphosphate, calcium carbonate, calcium pyrophosphate, trimagnesium phosphate, magnesium carbonate, etc. Mixtures of polishing agents may be used.

Hydrated alumina particularly the alpha-alumina trihydrate sold by Alcoa as C333, which has an alumina content of 64.9% by weight, a silica content of 0.008%, a ferric oxide content of 0.003%, and a moisture content of 0.37% at 110° C., and which has a specific gravity of 2.42 and a particle size such that 100% of the particles are less than 50 microns and 84% of the particles are less than 20 microns, is desirable. Other grades of hydrated alumina may, of course, be used.

The polishing material is generally present in amounts ranging from 10% to 75% by weight of the dental cream composition.

A fluorine-providing compound is present in the oral preparation. These compounds may be slightly soluble in water or may be fully water-soluble. They are characterised by their ability to release fluoride ions in water and by substantial freedom from reaction with other compounds of the oral preparation. Among these materials are inorganic metal and salts, for example, sodium fluoride, potassium fluoride, ammonium fluoride, lead fluoride, a copper fluoride such as cuprous fluoride, zinc fluoride, a tin fluoride such as stannous fluoride or stannous chlorofluoride, sodium fluorosilicate, ammonium fluorosilicate, sodium fluorozirconate, sodium monofluorophosphate, alumina mono- and difluorophosphate. Alkali metal and tin fluorides, such as sodium fluoride, stannous fluoride, sodium monofluorophosphate and mixtures thereof, are preferred. Mixtures of sodium fluoride and sodium monofluorophosphate are particularly desirable.

The amount of the fluorine-providing compound is dependent to some extent upon the type of compound, and its solubility but it is a non-toxic amount typically to release a maximum of about 1% by weight of the composition.

Any suitable minimum amount of such compound may be used, but it is preferable to employ sufficient compound release from about 0.005% to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05% to 1%. In the case of sodium monofluorophosphate, the compound may be present in an amount up to 7.6% by weight, more typically 0.76%. When present in mixture the ratio of sodium monofluorophosphate to sodium fluoride is desirably about 1:1 to 3:1 based on fluorine provided by each.

Suitable surface active or detersive material may be included in the dentifrice compositions. Such compatible materials are desirable to provide additional detersive, foaming and antibacterial properties depending upon the specic type of surface active material and are selected similarly. These detergents are water-soluble organic compounds usually, and may be anionic, non-ionic or cationic in structure. It is preferred to use the water-soluble non-soap or synthetic organic detergents usually. Suitable detersive materials are known and include, for example, the water-soluble salts or higher fatty acid monoglyceride monosulfate detergent (e.g. sodium coconut fatty acid monoglyceride monosulfate), higher alkyl sulfate (e.g. sodium lauryl sulfate), alkyl aryl sulfonate (e.g. sodium dodecyl benzene sulfonate, sodium coconut fatty acid ester of 1,2-dihydroxypropane sulfonate), aliphatic alcohol, ethoxylated sulfates and the like.

The dental cream composition may also contain at least one of the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-amino-propanoic acid and valine having about 12 to 16 carbons in the acyl group. N-lauroyl, myristoyl and palmitoyl sarcoside compounds provide optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, reference to "amino carboxylic acid compounds", "sarcoside", and the like refers to such compounds having a free carboxylic group or the water-soluble carboxylic salts.

Such materials are utilized in pure or substantially pure form. They should be as free as practical from soap or similar higher fatty acid material which tends to reduce the activity of these compounds. In usual practice, the amount of such higher fatty acid material is less than 15% by weight of the amide and insufficient to substantially adversely affect it, and preferably less than about 10% of the said amide material.

The various surface active materials may be used in any suitable amount, generally from 0.5 up to 10% by weight, and preferably from about 0.5 to 5% by weight of the dentifrice composition, with about 1.5 to 2% especially preferred.

For some purposes it may be desirable to include antibacterial agents in the compositions of the present invention. Typical antibacterial agents, which may be used in amounts of 0.01 to 5%, preferably 0.05 to 1.0%, by weight of the dentifrice composition include:
$N^1$-4(chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1-(lauryldimethylammonium)-8-(p-chlorobenzyldimethylammonium)octane dichloride;
5,6-dichloro-2-guanidinobenzimidazole;
$N^1$-p-chlorphenyl-$N^5$-laurylbiguanide;
5-amino-1,3-bis(2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavour and sweetening agent may together comprise from about 0.01 to 5% or more of the instant invention.

Various other materials may be incorporated in the dental creams of this invention. Examples thereof are colouring or whitening agents, preservatives, silicones, chlorophyll compounds and ammoniated materials such as urea, diammoniumphosphate and mixtures thereof. These adjuvants are incorporated in the instant compositions in amounts which do not substantially adversely affect the properties and characteristics, suitably selected and used in proper amount depending upon the particular type of preparation involved.

The dental composition should have a pH practical for use, ranging from acidic to alkaline, e.g. a pH of 4 to 10, preferably from 5 to 8 and most preferably from 6 to 7.5. The reference to the pH herein refers to a pH determination directly on a 25% aqueous slurry of the dental cream composition.

The swelling properties of both xanthan and alginate salt are such that their mixture can be premixed with the polishing agent and introduced simultaneously with an aqueous solution of humectant and other additives into a mixing apparatus, without resorting to heat. Such a preparation technique is described in Cosmetics, Science and Technology, Balsam and Sagarin, Wiley-Interscience, New York, 1972, Volume I, page 511. Alternatively, the xanthan-alginate mixture may be added directly to anhydrous humectant and then mixed with the other components.

The following examples are illustrative of the present invention. The amounts of the various ingredients are by weight unless otherwise indicated.

EXAMPLE 1

The following dental cream is prepared, deaerated and placed in aluminum toothpaste tubes.

|  | PARTS |
|---|---|
| Sorbitol (70%) | 30.00 |
| Glycerine | 18.00 |
| Silica containing combined alumina (Zeo 49 From J. M. Huber) | 18.00 |
| Silica thickening agent (Syloid 244 from W. R. Grace) | 5.00 |
| Sodium lauryl sulfate | 1.20 |
| Sodium monofluorophosphate | 0.76 |
| Sodium benzoate | 0.50 |
| Xanthan (Keltrol from Kelco) | 0.75 |
| Sodium alginate (Kelcosol) | 0.25 |
| Sodium saccharin | 0.20 |
| Flavour, colour, water | Q. S. to 100.00 |

Upon brushing the dental cream in the oral cavity in contact with teeth, quick dispersion is achieved with a desirable feeling of texture throughout the oral cavity, which is slow to drain away.

Similar results are obtained with 0.50 parts of xanthan and 0.50 parts of sodium alginate in the formula.

EXAMPLES 2 AND 3

The following dental creams provide quick dispersion and desirable mouth feel:

|  | 2 PARTS | 3 PARTS |
|---|---|---|
| Sorbitol (70%) | 16.00 | — |
| Glycerine | 8.00 | 22.00 |
| Tetrasodium pyrophosphate | — | 0.25 |
| Monobasic sodium phosphate | 0.26 | — |
| Sodium saccharin | 0.20 | 0.20 |
| Sodium benzoate | — | 0.50 |
| Sodium monofluorophosphate | 0.76 | 0.76 |
| Hydrated alumina | 52.00 | — |
| Dicalcium phosphate dihydrate | — | 48.76 |
| Xanthan | 0.75 | 0.75 |
| Sodium alginate | 0.25 | 0.25 |
| Sodium lauryl sulfate | 1.20 | 1.20 |
| Flavour, water | Q.S. to 100 | Q.S. to 100 |

EXAMPLES 4 AND 5

The following dental creams provide quick dispersion and desirable mouth feel:

|  | 4 PARTS | 5 PARTS |
|---|---|---|
| Sorbitol (70%) | 17.00 | — |
| Glycerine | 10.00 | 22.00 |
| Tetrasodium pyrophosphate | — | 0.50 |
| Sodium saccharin | 0.20 | 0.19 |
| Sodium benzoate | 0.50 | — |
| Sodium monofluorophosphate | 0.76 | 0.76 |
| Insoluble sodium metaphosphate | 39.35 | — |
| Anhydrous dicalcium phosphate | 5.00 | — |
| Hydrated alumina | 1.00 | — |
| Calcium carbonate | — | 40.50 |
| Titanium dioxide | 0.40 | — |
| Xanthan | 0.75 | 0.75 |
| Sodium alginate | 0.25 | 0.25 |
| Sodium lauryl sulfate | 0.25 | 0.25 |
| Flavour, water | Q.S. to 100 | Q.S. to 100 |

EXAMPLE 6

The following dental cream has incorporated therein 1.00 part of the gel compositions indicated below:

|  | PARTS |
|---|---|
| Sorbitol (70%) | 30.00 |
| Glycerine | 18.00 |
| Silica containing combined alumina | 18.00 |
| Silica thickener | 5.00 |
| Sodium lauryl sulfate | 1.20 |
| Sodium monofluorophosphate | 0.76 |
| Sodium benzoate | 0.50 |
| Sodium saccharin | 0.20 |
| Flavour, colour, water | Q.S. to 99.00 |

Gelling Agent Compositions Incorporated into above Dental Cream:

A. 1% Xanthan
B. 1% Sodium Alginate
C. 1% Carbopol 940 (Carboxyvinyl polymer available from B. F. Goodrich).

The viscosities of the dental creams containing gelling agents A, B and C are determined per Brookfield LVT, Spindle #2 at room temperature with 1 part dental cream in 2.5 parts of water. The following viscosities are obtained at the indicated speeds:

|   | | SPEED & VISCOSITY (IN CENTIPOISES-CPS) | | | | |
|---|---|---|---|---|---|---|
|   | | 3 | 6 | 12 | 30 | 60 |
| A. | (1% Xanthan) | | | | | |
|   | First test | 1500 | 1000 | 663 | 365 | 230 |
|   | Second test | 1400 | 950 | 625 | 350 | 225 |
| B. | (1% Sodium Alginate) | 100 | 75 | 75 | 50 | 48 |
| C. | (1% Carbopol 940) | 150 | 150 | 125 | 85 | 63 |

The pseudoplasticity of dental creams with gelling agent A (1% xanthan) is such that they are unduly thick and stringy and not subject to ready dispersion in the oral cavity.

The pseudoplasticity of dental creams with gelling agents B and C (1% Sodium alginate and 1% Carbopol 940) is such that they are thin and water-like.

Further Gelling Agent Compositions Incorporated into above Dental Cream:

D. 0.75% xanthan; 0.25% sodium alginate
E. 0.50% xanthan; 0.50% sodium alginate
F. 0.25% xanthan; 0.75% sodium alginate The viscosities of the dental creams are determined in the manner indicated above with the following results:

|   | | SPEED & VISCOSITY (IN CPS) | | | | |
|---|---|---|---|---|---|---|
|   | | 3 | 6 | 12 | 30 | 60 |
| D. | (0.75% xanthan; 0.25% sodium alginate) | 900 | 650 | 450 | 270 | 180 |
| E. | (0.50% xanthan; 0.50% sodium alginate) | 500 | 400 | 288 | 190 | 135 |
| F. | (0.25% xanthan; 0.75% sodium alginate) | 200 | 175 | 175 | 120 | 93 |

The pseudoplasticity of dental creams with gelling agents D and E (0.75% xanthan-0.25% sodium alginate and 0.50% xanthan and 0.50% sodium alginate, respectively) is quite desirable as is the ease of dispersion and these characteristics of the dental cream with gelling agent D is excellent. The compositions have a fine gel consistency and do not have the stringiness associated with the dental creams containing gelling agent A (1% xanthan). The dental cream containing gelling agent F (0.25% xanthan and 0.75% sodium alginate) has improved viscosity and dispersion characteristics over the dental creams containing gelling agents B and C (1% sodium alginate and 1% Carbopol 940).

Further Gelling Agent Compositions Incorporated into above Dental Cream:

G. (0.75% xanthan; 0.25% Carbopol 940)
H. (0.50% xanthan; 0.50% Carbopol 940)
I. (0.25% xanthan; 0.75% Carbopol 940)

The viscosities of these dental creams are determined in the manner indicated above with the following results:

|   | | SPEED & VISCOSITY (IN CPS) | | | | |
|---|---|---|---|---|---|---|
|   | | 3 | 6 | 12 | 30 | 40 |
| G. | (0.75% xanthan; 0.25% Carbopol 940) | 1750 | 1225 | 800 | 450 | 288 |
| H. | (0.50% xanthan; 0.50% Carbopol 940) | 1700 | 1125 | 725 | 415 | 275 |
| I. | (0.25% xanthan; 0.75% Carbopol 940) | 950 | 650 | 438 | 260 | 178 |

The pseudoplasticity of each of the dental creams with gelling agents G and H (0.75% xanthan and 0.25% Carbopol 940 and 0.50% xanthan and 0.50% Carbopol 940) is such that they are unduly thick and stringy and not subject to ready dispersion in the oral cavity, much like the dental cream containing gelling agent A (1% xanthan). When Carbopol 940 is present, only when xanthan is just 25% of the gel mixture as in gelling agent I, does the dental cream have desirable pseudoplasticity character.

The foregoing comparative experiments demonstrate that even though alginate and carboxyvinyl behave similarly as gelling agents when used alone (B and C), when they are mixed with xanthan, the xanthan-alginate mixture has desirable pseudoplasticity over a broad range of mixture ratios (D, E and F) and does not have the disadvantages of xanthan when used alone (A). On the other hand, xanthan-carboxyvinyl polymer gives desirable pseudoplasticity at a 3:1 ratio (I) but has the disadvantages of xanthan alone when greater amounts of xanthan are present in the mixture (G and H).

The invention has been described with respect to various illustrative examples thereof but is not intended to be limited to these examples since one may readily substitute equivalents thereto without going outside the scope of the invention described.

I claim:

1. A non-stringy, easily dispersible dental cream overcoming the stringy, difficult to disperse quality imparted by xanthan comprising about 20–80% by weight of a liquid vehicle phase comprising water and humectant and about 0.2–5% by weight of a gel vehicle phase and dispersed therein about 10–75% of a water-insoluble dentally acceptable polishing agent, said gel vehicle containing a weight ratio of about 3:1 to 1:3 of xanthan to alginate salt.

2. The dental cream claimed in claim 1 wherein said weight ratio is about 3:1 to 1:1 of xanthan to alginate salt.

3. The dental cream claimed in claim 2 wherein said dental cream contains about 0.75% by weight of xanthan and about 0.25% by weight of alginate salt.

4. The dental cream claimed in claim 1 wherein said gel vehicle phase is present in amount of about 0.5–2% by weight.

* * * * *